United States Patent [19]

Bushaw

[11] Patent Number: 4,599,512

[45] Date of Patent: Jul. 8, 1986

[54] LASER INDUCED PHOSPHORESCENCE URANIUM ANALYSIS

[75] Inventor: Bruce A. Bushaw, Kennewick, Wash.

[73] Assignee: The United States of America as represented by the United States Department of Energy, Washington, D.C.

[21] Appl. No.: 503,130

[22] Filed: Jun. 10, 1983

[51] Int. Cl.$^4$ ............................................. G01N 21/64
[52] U.S. Cl. ...................................... 250/253; 356/318
[58] Field of Search .................... 250/461.1, 253, 255, 250/459.1, 458.1; 356/318

[56] References Cited

U.S. PATENT DOCUMENTS

| | | | |
|---|---|---|---|
| 4,198,568 | 4/1980 | Robbins et al. | 250/459.1 |
| 4,236,071 | 11/1980 | Chimenti | 250/253 |
| 4,239,964 | 12/1980 | Robbins et al. | 250/255 |
| 4,365,153 | 12/1982 | Seigel et al. | 250/461.1 |
| 4,464,568 | 8/1984 | Brown et al. | 250/461.1 |

OTHER PUBLICATIONS

Felix, "Breakthrough in Uranium Bioassay", Health Physics Society Newsletter, Jan. 1983, p. 3.
Robbins, "No Breakthrough", Health Physics Society Newsletter, Mar. 1983, p. 4.
Bushaw, "Author's Response", Health Physics Society Newsletter, Mar. 1983, p. 5.
Benson et al, "Concentration and Temperature Quenching of the Excited State of the Uranyl Ion in Aqueous Solution by Laser Flash Photolysis", Chem. Phys. Letters, vol. 35 (2), Sep. 1, 1975. pp. 195–197.

Primary Examiner—Carolyn E. Fields
Attorney, Agent, or Firm—Robert Southworth, III; Judson R. Hightower

[57] ABSTRACT

A method is described for measuring the uranium content of aqueous solutions wherein a uranyl phosphate complex is irradiated with a 5 nanosecond pulse of 425 nanometer laser light and resultant 520 nanometer emissions are observed for a period of 50 to 400 microseconds after the pulse. Plotting the natural logarithm of emission intensity as a function of time yields an intercept value which is proportional to uranium concentration.

1 Claim, 3 Drawing Figures

LASER INDUCED PHOSPHORESCENCE URANIUM ANALYSIS

The U.S. Government has rights in this invention pursuant to Contract No. DE-AC06-76RL01830 between the U.S. Department of Energy and the Battelle Memorial Institute.

BACKGROUND OF THE INVENTION

The invention relates generally to the analysis of aqueous solutions for uranium content and, more particularly to a method for analyzing aqueous solutions for uranium content employing laser exitation phosphorimetry.

Conventional fluorometric methods of analysis for uranium in aqueous samples suffer from a lack of sensitivity, limited precision, and complicated time-consuming preparative chemistry. For example, the routine analysis of urine from uranium content may require a one liter sample, involve a multiple step preliminary chemical procedure, and only be able to detect down to 5 parts per billion uranium. In addition, quenching by various inorganic ions and spurious fluorescing by organics will give false results.

It is accordingly an object of the invention to provide a method for analyzing the uranium concentration in aqueous solutions with little or not chemical pretreatment.

It is also an object of the invention to provide an instrumental method for the correction of sample matrix interferences while analyzing uranium concentration.

It is a further object of the invention to provide a method for uranium analysis with improved detection limits, precision, and accuracy.

Other object, advantages and novel features of the invention will be apparent to those of ordinary skill in the art upon examination of the following detailed description of a preferred embodiment of the invention.

SUMMARY OF THE INVENTION

A method is provided for measuring uranium in aqueous solution wherein a uranyl phosphate complex is irradiated with a 5 nanosecond pulse of 425 nanometer laser light and resultant 520 nanometer emissions are observed for a period about 50 to 400 microseconds after the pulse. Kinetic analysis of the time resolved emission is used to correct for matrix quenching.

DESCRIPTION OF A PREFERRED EMBODIMENT

Figure 1:
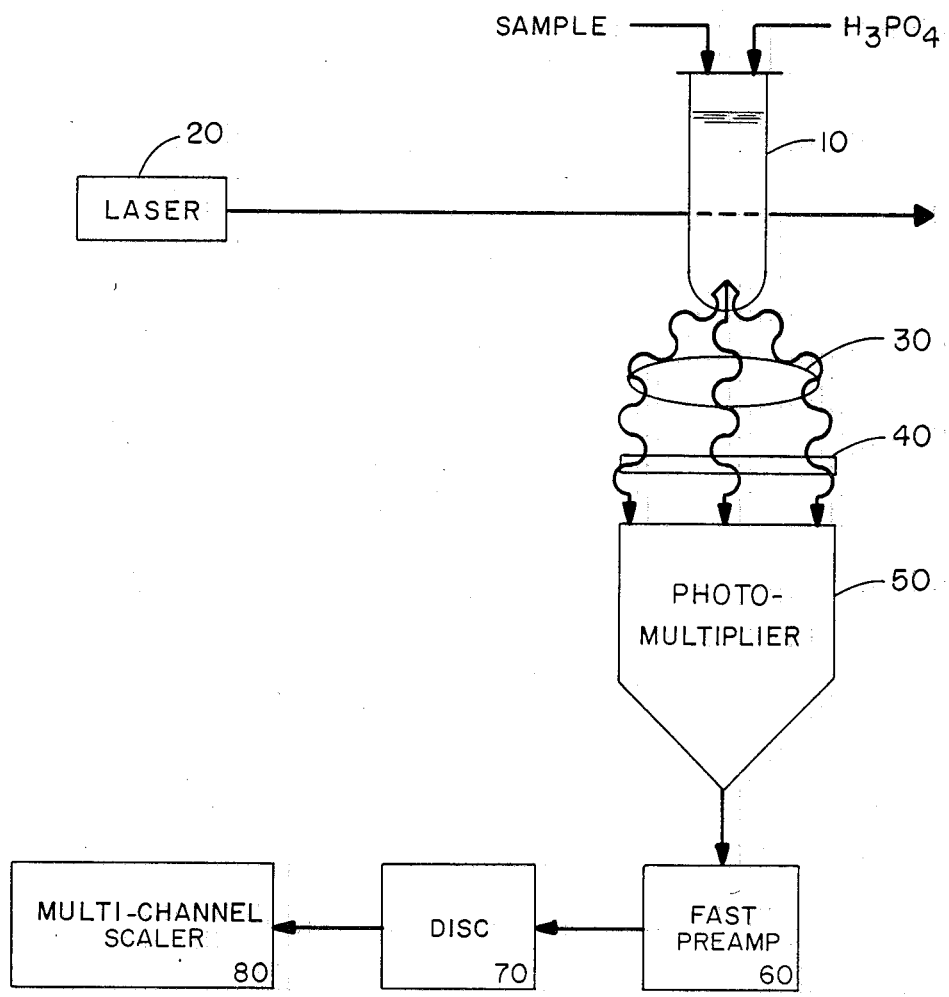
FIG. 1 illustrates an apparatus suitable for practicing the method of the invenion.

Laser induced phosphorescence may be used to determine the uranium concentration of aqueous solutions using the following technique (referring to FIG. 1). A 10 ml aliquot of a suitable sample is added to 1.5 ml of 1 molar phosphoric acid solution in a standard 10 mm path fused silica fluorescence cell 10. The addition of phosphoric acid produces a phosphorescent uranyl phosphate complex. Suitable samples such as drinking or surface water may be directly analyzed without chemical pretreatment. Pretreatment by $HNO_3/HClO_4$ digestion is used for the analysis of brine and sea waters, urine and other samples of biological origin. The sample is then excited with laser light produced by a nitrogen laser pumped broad band dye laser 20 (using stilbene 420 dye). The laser is operated at 425 nanometers with a bandwidth of 15 nanometers and has a peak power of about 50 kilowatts with a 5 nanosecond pulse duration.

The induced emissions are collected at right angles to the laser excitation with the combination of a spherical mirror and lens 30. The collected emissions are passed through a 520 nanometer interference filter 40 and are observed with a dry ice cooled photomultiplier 50 (RCA 31034). The photomultiplier is used in a photon counting mode with the anode signal processed by a fast preamplifier 60 and a discriminator 70. The scaler output of the discriminator is then used for the actual counting. Photon counting in a time resolved mode is accomplished with a multichannel scaler 80 using a 10 microsecond per channel dwell. The multichannel scaler sweep is repetitively triggered by the firing of the laser and a summation of the number of counts in each channel is made for a specified number of laser shots.

The induced phosphorescence may be masked by laser and raman scattering, prompt flourescing organic species, and matrix quenching. The scattering and prompt fluorescence may be screened out by ignoring those photons generated in the first 50 microseconds after the laser pulse. The basis for correction of matrix quenching is derived directly from the photokinetics of the emitting state. If a given population of uranyl phosphate is placed in the emitting excited state then its evolution may be described by the simple first order differential equation.

$$dU/dt = (K_p + K_q)U \quad (1)$$

Where U is the concentration of uranium in the emitting excited state $K_p$ is the intrinsic rate constant for phosphorescence and $K_q$ is a summation for all the various channels of radiationless deactivation. The integrated form of this equation is:

$$U(t) = U(O) exp\ (-(K_p = K_q)t) \quad (2)$$

which can be linearized to $$ln\ (U(t)) = ln\ (U(O)) - (K_p + K_q)t \quad (3)$$

Thus, plotting the natural log of the emission intensity as a function of time yields an intercept of $ln(U(O))$, a direct measurement of the initially created population, independent of matrix quenching effects.

Figure 2:
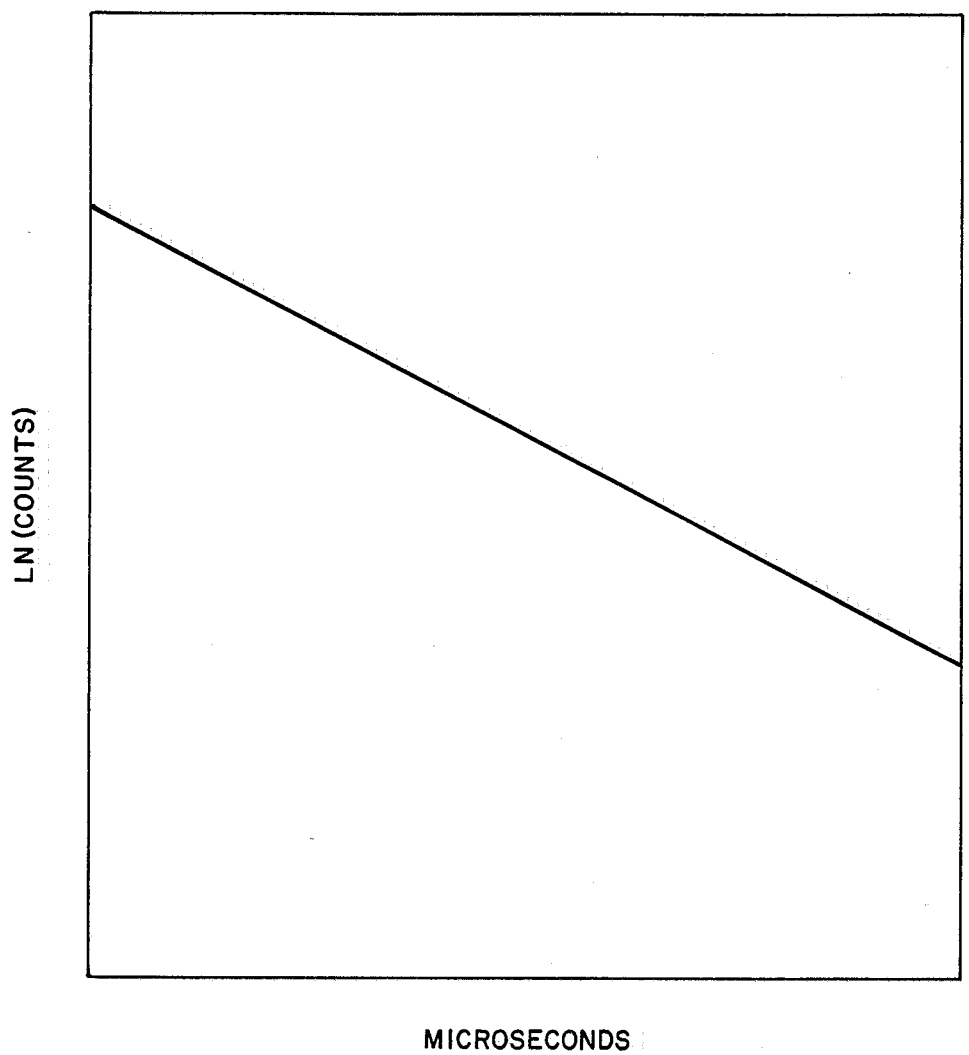
FIG. 2 illustrates a least squares curve fitting of the natural logarithm of counting data.
Figure 3:
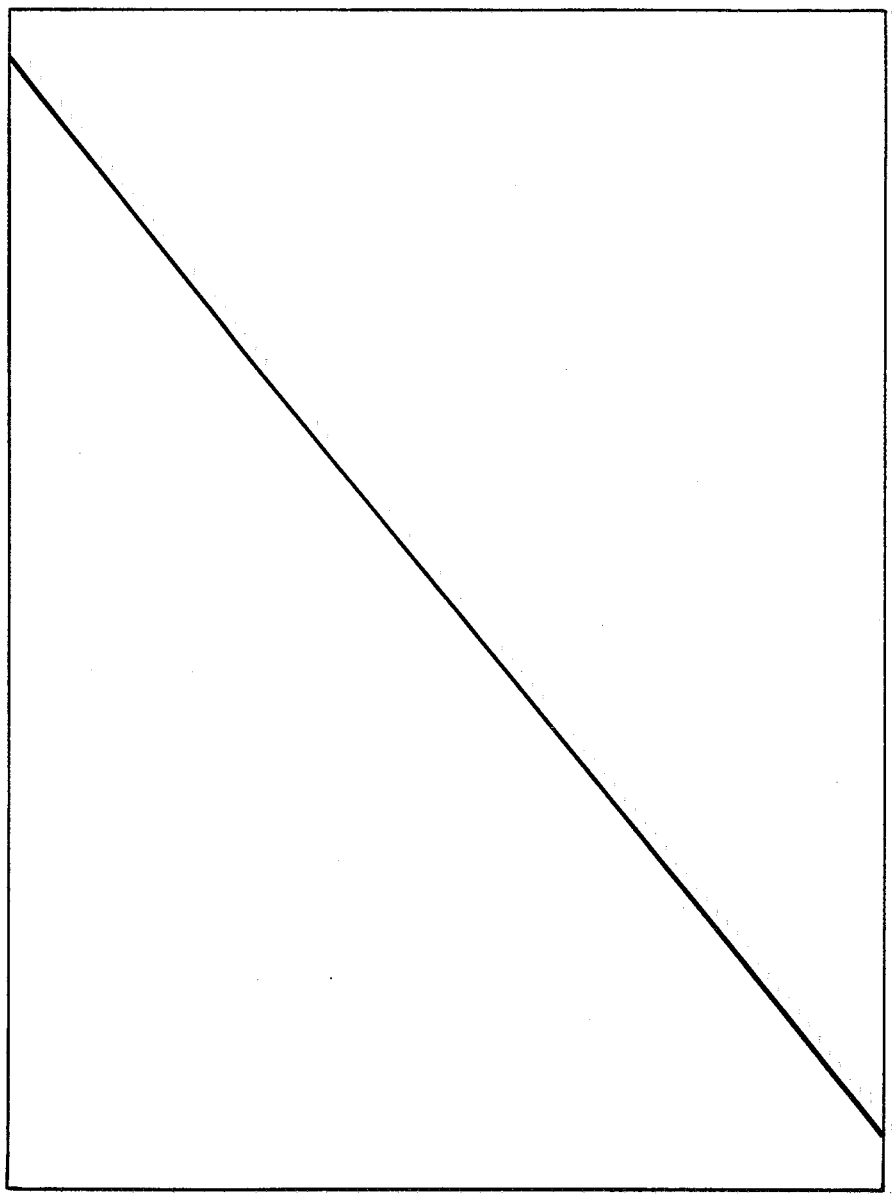
FIG. 3 illustrates a standard calibration curve.

For actual data reduction, the background spectrum is first subtracted from the sample spectrum. Then the natural logarithm of the count in each channel is calculated and least squares fitting according to equation (3) performed. The fitting is usually carried out over channels 5 to 40 (equivalent to 50 to 400 microseconds after the laser fires). Such a fitting is illustrated in FIG. 2 wherein the natural logarithm of the counts is plotted against the time elapsed in microseconds. The least squares curve fit results in an intercept of ln $(U(O))$ which is used in the final analytical equation.

$$U = (exp(b)/(S_b - b_s))\ (d_f/m_s) \quad (4)$$

Where $S_b$ is the integrated count from the background spectrum, $b_s$ and $m_s$ are the intercept and slope for a standard calibration curve and $d_f$ is the dilution factor for the sample volume added to the phosphoric acid solution. This standard calibration curve is illustrated in FIG. 3.

It has been found that the present invention may be used to detect uranium concentrations as low as 1 part per trillion.

The foregoing description of a preferred embodiment of the intention has been presented for purposes of illustration and is not intended to be exhaustive or to limit the invention to the precise form disclosed. It was chosen and described in order to best explain the principles of the invention and their practical application to thereby enable others skilled in the art to best utilize the invention in various embodiments and with various modifications as are suited to the particular use described. It is intended that the scope of the invention be defined by the claims appended hereto.

I claim:

1. A method for measuring uranium in aqueous solution comprising:
    (a) adding phosphoric acid to a sample to convert any uranium present to a uranyl phosphate complex;
    (b) irradiating the sample with a laser light pulse having a wavelength of 425 nanometers, a bandwidth of 10 nanometers, peak power of 50 kilowatts, and pulse duration of 5 nanoseconds;
    (c) observing any resultant emissions at a wavelength of 520 nanometers at timed intervals of 10 microseconds duration during the time from 50 to 400 microseconds after the laser light pulse;
    wherein the natural logarithm of the emission intensity observed in step (c) is plotted as a function of time yielding an intercept value which is directly proportional to uranium concentration independent of variations in absolute emission intensity which are caused by matrix quenching or by the temperature of the aqueous solution.

* * * * *